United States Patent [19]

Stack et al.

[11] Patent Number: 4,905,689

[45] Date of Patent: Mar. 6, 1990

[54] METHOD OF USING A LASER CATHATER

[76] Inventors: Richard S. Stack, 6913 Falcon Bridge Rd., Chapel Hill, N.C. 27514; Myron L. Wolbarsht, 1435 Acadia St., Durham, N.C. 27701

[21] Appl. No.: 190,053

[22] Filed: May 4, 1988

Related U.S. Application Data

[62] Division of Ser. No. 66,346, Jun. 25, 1988, Pat. No. 4,854,315.

[51] Int. Cl.$^4$ .............................................. A61N 5/06
[52] U.S. Cl. ...................................... 606/3; 128/398; 606/7; 606/15
[58] Field of Search ................ 128/303.1, 303.11, 341, 128/362, 395, 397, 398; 350/96.34

[56] References Cited

U.S. PATENT DOCUMENTS

| | | | |
|---|---|---|---|
| 4,341,873 | 7/1982 | Robinson et al. | 350/96.34 |
| 4,449,532 | 5/1984 | Story | 128/341 |
| 4,583,539 | 4/1986 | Karlin et al. | 128/303.1 |

Primary Examiner—Lee S. Cohen
Assistant Examiner—David Shay
Attorney, Agent, or Firm—Cushman, Darby & Cushman

[57] ABSTRACT

A laser catheter for removing atherosclerotic plaque. The distal end of the laser catheter, in addition to including a distal port for dye injection and preferably a steerable or at least movable guide wire, includes a smoothly tapered forward face with a sapphire, ruby, diamond or the like window for directing a mid-infrared laser beam centripedally toward a targeted plaque structure. A mid-infrared laser beam, preferably a erbium YAG or HF laser, is conducted through the catheter to abate plaque. A second catheter, substantially identical to the first catheter can slidably disposed about the first catheter so as to provide a tiered laser catheter. Thus, the smaller catheter can target plaque in the most constricted regions of the vessel and can then be advanced into the smaller diameter region wile bringing the second, larger catheter into engagement with a larger diameter packed portion thereby enable the irradiation, and ablation of the same.

5 Claims, 2 Drawing Sheets

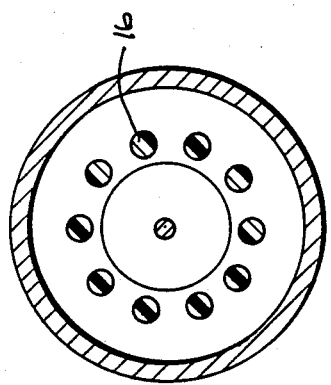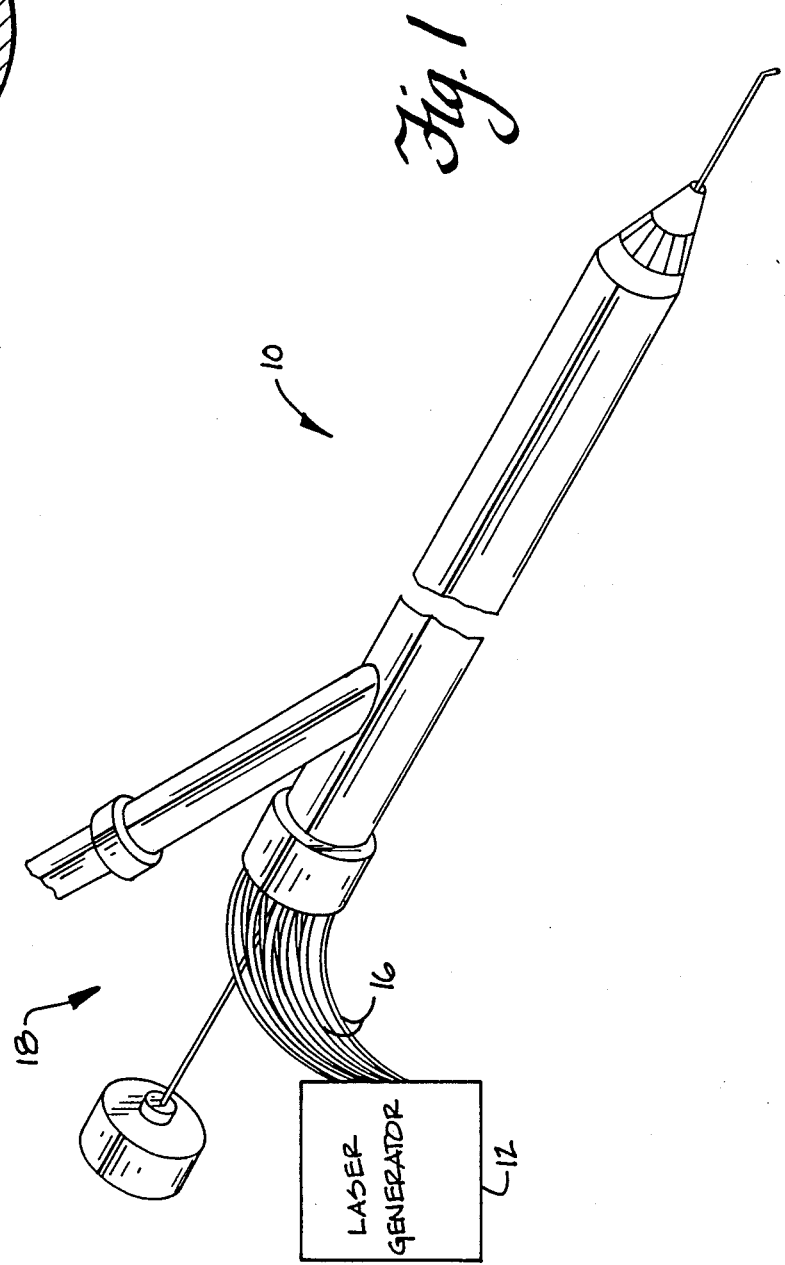

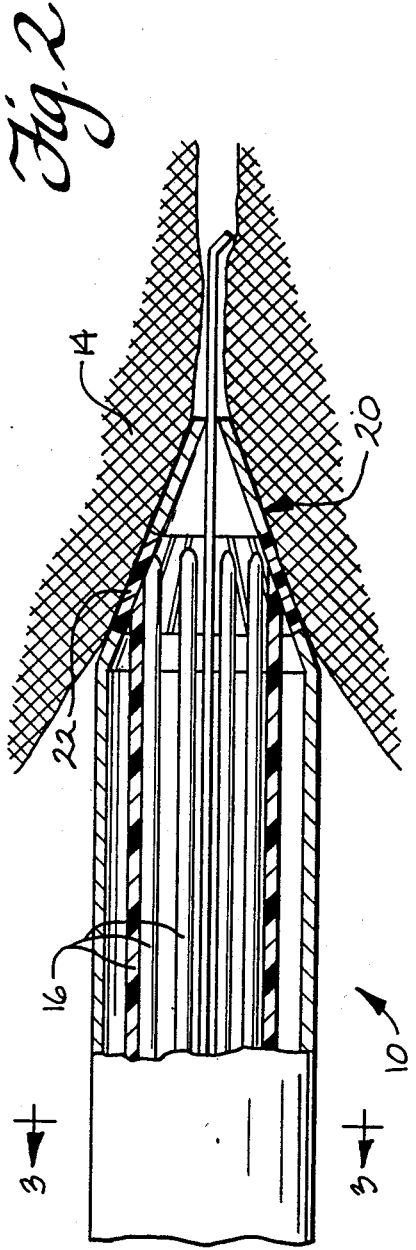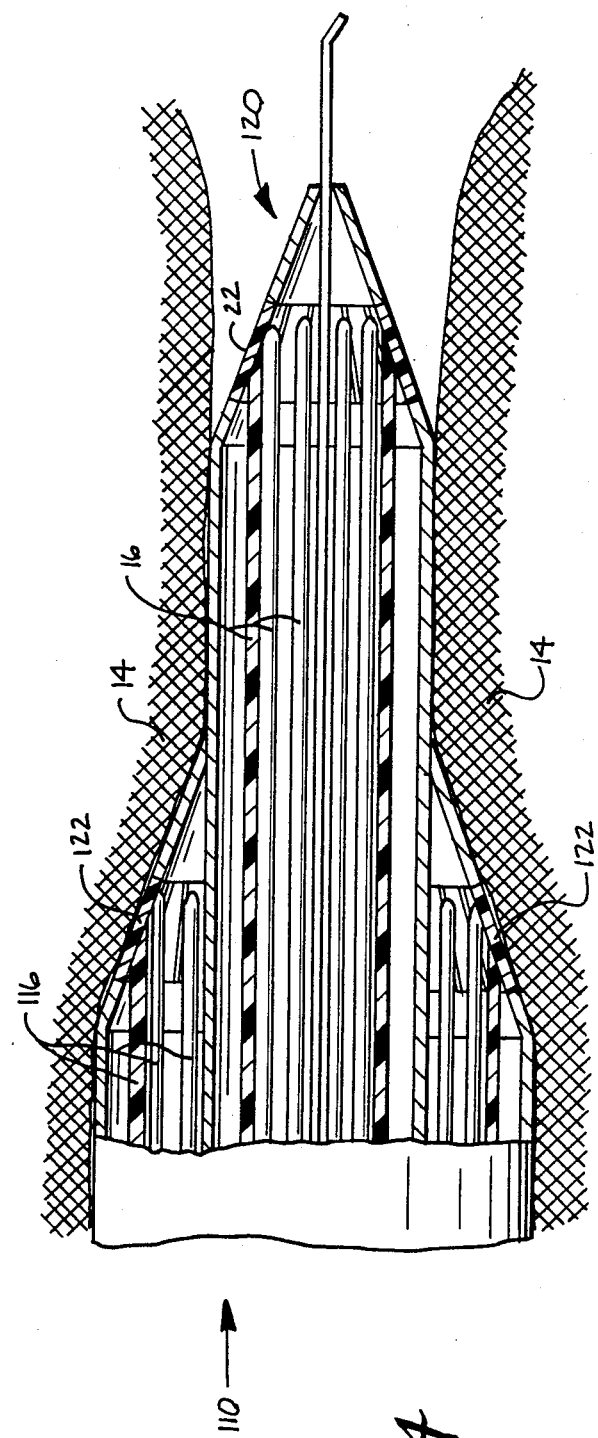

METHOD OF USING A LASER CATHETER

This is a division of application Ser. No. 066,346, filed June 25, 1988, now Pat. No. 4,854,315.

BACKGROUND OF THE INVENTION

The present invention relates to laser catheters and, more particularly, to a laser catheter for removing athereosclerotic plaque.

The use of laser catheters for removing obstructions from blood vessels and the like is known, generally. However, these catheters employ standard visable light lasers which have a number of disadvantages when used within blood vessels. More particularly, when such a standard visible laser is used, the material being destroyed is heated to vaporization/combustion. Because the targeted material is heated to such an extent in order to be destroyed, healthy tissue surrounding the targeted tissue is also heated and can be charred and/or otherwise loose its structural integrity. Further, because it is difficult to control the direction of the laser beam of standard visible lasers within the vessel, perforation of the blood vessel wall is likely.

There have been attempts at controlling the direction in which the laser beam is emitted and hence the material impinged thereby. However, these attempts have primarily lead to providing catheters wherein the laser beam is directed radially of the vessel to impinge upon a particular targeted portion of the athereosclerotic plaque. Directing the laser beam towards the side wall of the blood vessel, however, can easily lead to perforation of the blood vessel and/or weakening of the vessel wall due to the excessive heating of the healthy tissue forming the wall.

Other attempts have also been made, such as injecting luminescent dyes into the blood stream in order to more readily recognize the targeted portion of the vessel and to thereby minimize the likelihood of damaging healthy tissue. However, the heat of the laser will still cause damage to the healthy tissue.

Thus, while the use of lasers within blood vessels initially appeared to be promising, doctors and researchers have become discouraged at the uncontrollability of currently available visable light laser catheters. Indeed, even when a standard visible laser is used, for example, during open heart surgery it has been found that there is often rapid restenosis of the targeted portions of the vessel and, despite greater accuracy in terms of targeting the laser, the exposure of healthy tissue to excessive heat still leads to deleterious results.

Another attempt at controlling lasers applied to blood vessels is known as the excimer laser which is a combination of argon fluoride or krypton chloride and a rare earth gas. This combination forms a laser beam having a very short wavelength and hence photons of very high energy. Thus, the excimer laser enables the disintegration of targeted tissue before the vaporization stage and can yield relatively pure disintegration without excessive thermal damage to otherwise healthy tissue.

While the thermal damage is reduced with the excimer laser, there is still a great deal of heat transmitted which can destroy enzymes and the like in the surrounding tissue. Further, because the excimer laser utilizes far ultraviolet rays, questions have been raised as to whether this device will increase the risk of cancerous tissue development. Finally, the photon energy of the excimer laser is so high that it is very difficult if not impossible to transmit the laser effectively through known fibers.

SUMMARY OF THE INVENTION

It is an object of the present invention to overcome the deficiencies of known laser catheters, set forth above. More particularly, it is an object of the present invention to provide a laser catheter which can destroy athereosclerotic plaque without excessively heat damaging healthy tissue adjacent the targeted portion of the vessel. It is also an object of the present invention to provide a laser catheter which can destroy targeted athereosclerotic plaque while minimizing the likelihood of perforating the blood vessel.

The foregoing objects are realized in accordance with the present invention by providing a mid-infrared laser beam conducting catheter which can be directed centripedally toward a targeted plaque stricture. The laser is preferably an erbium YAG or HF laser which generates a pulsed laser in the mid-infrared range so that the depth of destruction by the laser can be controlled. The distal end of the catheter preferably includes a port for dye injection and a steerable or at least movable guide wire. Further, the distal end of the catheter has a smoothly tapered forward face with one or more window(s) of sapphire, diamond or the like for directing a mid-infrared laser beam centripedally towards a targeted plaque stricture. The provision of a tapered forward face provides the additional advantage that the catheter utilizes the Dotter Effect in that it will guide the catheter through constricted portions while deflecting plaque so that the tapered distal face, including the laser window(s), will abutt the plaque of the most constricted portion of the vessel. Thus, the distal end will slightly expand the plaque and enable effective ablation of the plaque by the laser beam(s) emitted through the window(s). Because depth of plaque destruction can be controlled and the depth of transmitted heat can be controlled with the pulsed laser, there will be no perforation of the blood vessel. Thus, the likelihood of subsequent aneurysm and/or heat destruction of adjacent tissues is minimized.

Other objects, features and characteristics of the present invention, as well as the methods of operation and functions of the related elements of the structure, and the combination of parts and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

FIG. 1 is a perspective view of a laser catheter assembly formed in accordance with the present invention;

FIG. 2 is a side elevational view, partly broken away and in cross-section for clarity, showing a laser catheter formed in accordance with the present invention disposed within a blood vessel in engaging relation to a targeted portion of athereosclerotic plaque;

FIG. 3 is a cross sectional view taken along line 3—3 of FIG. 2; and

FIG. 4 is a side elevational view of a second embodiment of the laser catheter assembly formed in accordance with the present invention.

DETAILED DESCRIPTION OF THE PRESENTLY PREFERRED EXEMPLARY EMBODIMENTS

Referring to FIGS. 1 and 2, a laser catheter 10 formed in accordance with the present invention is adapted to receive a laser beam from a erbium YAG or HF laser 12 (shown schematically in FIG. 1). Thus, the laser beam directed against the athereosclerotic plaque 14 (FIG. 2) is a pulsed beam in the mid-infrared range having a wavelength of between about 2.6 and about 2.9 microns. The laser beam is directed and focused into fiber optic cables 16 or the like which extend from the proximal-most portion 18 of the laser catheter 10 to the distal end 20 thereof. The fiber optic cables 16 provided for the mid-infrared pulsed laser of the present invention are not conventional fiber optics but, rather, are fiber optic cables formed from, for example, zirconium fluoride or zirconium chloride which can conduct the mid-infrared laser beam without a significant energy loss along the length thereof.

As can be seen, the distal end 20 of laser catheter 10 is tapered and includes terminal or distal windows 22 for the emission of the laser beam(s) conducted through fiber optic cables 16 disposed in the catheter. In the illustrated embodiment, distal windows 22 are disposed circumferentially of the end of the laser catheter as are fiber optic cables 16 which extend the length of the catheter (FIG. 3). In this manner, the laser beam can be circumferential directed to the athereosclerotic plaque 14. Of course, where the plaque is disposed primarily on a particular circumferential portion of the vessel, a catheter could be provided having fiber optics and distal window(s) at a corresponding circumferential portion thereof. In the alternative, means can be provided to control which fiber optic cables conduct the mid-infrared laser beam for a given plaque removing procedure.

Distal windows 22 provided at the distal end 20 of catheter 10, like fiber optic cables 16, must be formed of a particular material that can pass the mid-infrared laser beam. In accordance with a preferred embodiment of the present invention, the distal windows are formed from sapphires, rubies or diamonds. Of course, the particular material provided for the distal window(s) as well as for the fiber optic cables which extend the length of the catheter will become apparent to the ordinary artisan upon reviewing this disclosure.

Referring to FIG. 2, the distal end of the catheter formed in accordance with the present invention is tapered. In this manner the Dotter Effect can be employed in the plaque destroying procedure. More particularly, as laser catheter 10 is advanced to a point adjacent a stenotic region of the artery, the distalmost portion 20 of catheter 10 will enter the most constricted portion of the vessel. As the catheter is advanced further, the plaque 14 will be dilated slightly adjacent the forward end of the catheter so that the terminal windows 22 can be brought into abutting relation with the plaque 14 disposed on the vessel walls. The laser 12 is then activated so as to ablate the material in the immediate vicinity of distal windows 22.

The plaque 14 adjacent the distal end 22 of the catheter is thus destroyed so that the laser catheter 10 can be advanced further. However, because the laser beam is pulsed and has a wavelength in the mid-infrared range, the depth of ablation by the laser is limited, destroying plaque only immediately in front of the distal end 20 of catheter 10. The catheter can then be advanced further into the vessel to again come into abutting relation to plaque 14 on the vessel walls and the laser 12 can again be activated so as to ablate plaque 14 distally thereof.

The foregoing procedure is repeated until a desired circumferential portion of the plaque is removed from within the vessel. If more of the plaque, for example at a greater radius must be removed, the laser catheter can be removed and replaced by a laser catheter formed in accordance with the present invention but having a greater diameter than the first catheter. In the alternative, a second laser catheter 110, as shown in FIG. 4, can be slid along the length of the first laser catheter 10 to the site of a stenotic lesion. More particularly, the second laser catheter 110 has fiber optic conductors 116, for example, formed of zirconium fluoride or zirconium chloride which terminate adjacent distal windows 122. Again, in the illustrated embodiment, the fiber optics 116 and windows 122 disposed at the distal end 120 of catheter 110 are arranged in a circumferential manner. However, it is to be understood that fiber optics 116 as well as distal windows 122 can be limited to a particular circumferential portion of laser catheter 110 if the targeted portion of the athereosclerotic plaque 14 is limited to a given circumferential portion of the blood vessel.

As is apparent from the foregoing discussion, after the first laser catheter 10 has been utilized to ablate a given diameter of the targeted plaque 14 and has been advanced beyond the stricture, the second catheter 110 is advanced until it is in abutting relation to the plaque 14. A laser beam is then generated and directed down the fiber optic cables 16 of the second laser catheter 110 to ablate plaque 14 at a second radius in the vessel, larger that the radius of ablasion of the first catheter 10. In the alternative, the second catheter 110 can be disposed immediately proximally of the first catheter 10 so that a smooth taper from the first catheter 10 to the second catheter 110 can be provided. Thus, the catheters can be urged together into abutting relation to the plaque 14 such that the plaque is abutted by both the first distal window(s) 22 and the second distal window(s) 122. Laser beams can be then directed to both the first fiber optic cable(s) 16 and the second fiber optic cable(s) 116 to thereby simultaneously ablate plaque 14 at first and second radii and thereby effectively ablate a large circumferential portion of plaque 14 and open the constricted portion of the vessel.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of removing athereosclerotic plaque from the interior of a blood vessel comprising:
   providing a laser catheter including a tubular main body member having a distal end and a proximal end, said distal end having a smoothly tapered forward face; laser conducting means for conducting a laser beam from the proximal end of said main body member to the distal end thereof; and window means mounted to said smoothly tapered forward face for passing said laser beam through said distal end to thereby impinge said laser beam on a material to be removed;

inserting said laser catheter into a blood vessel and guiding said laser catheter to the locus of a material to be removed;

urging said tapered forward face into engagement with the material to be removed;

generating a pulsed laser beam in the mid-infrared range proximally of said tubular main body member;

conducting said laser beam through said conducting means from the proximal end of said main body member to the distal end thereof; and impinging said pulsed mid-infrared laser beam on the material within said blood vessel to thereby remove said material from the interior of said blood vessel.

2. A method as in claim 1, wherein said step of generating a pulsed laser beam in the mid-infrared range comprises generating a pulsed laser beam with an erbium YAG laser.

3. A method as in claim 1, wherein said step of generating a pulsed laser beam in the mid-infrared range comprises generating a pulsed laser beam with a HF laser generator.

4. A method as in claim 1, wherein said step of conducting said laser beam comprises conducting said laser beam through at least one fiber optic cable disposed circumferentially in said main body member of said laser catheter.

5. A method as in claim 1, further comprising the step of providing a second laser catheter including a second tubular main body member having a distal end and a proximal end, said distal end having a smoothly tapered forward face; laser conducting means for conducting a laser beam from the proximal end of said second tubular main body member to the distal end thereof; and window means mounted to said smoothly tapered forward face for passing said laser beam through said distal end to thereby impinge said laser beam on the material to be removed;

circumferentially and slidably mounting said second laser catheter on said tubular main body member;

inserting said second laser catheter into the blood vessel and guiding said second laser catheter to the locus of the material to be removed;

urging said tapered forward face of said second laser catheter into engagement with the material to be removed;

generating a pulsed laser beam in the mid-infrared range proximally of said second tubular main body member;

conducting said laser beam through said conducting means from the proximal end of said second tubular main body member to the distal end thereof; and impinging said pulsed mid-infrared laser beam on the material within said blood vessel to thereby remove said material from the interior of said blood vessel at a second radius, greater than a radius at which material is removed by said tubular main body member.

* * * * *